United States Patent [19]

Cain et al.

[11] Patent Number: 5,247,086
[45] Date of Patent: Sep. 21, 1993

[54] PROCESS FOR THE SYNTHESIS OF 5-[(SUBSTITUTED AMINO]-8-[PHENYL OR SUBSTITUTED-PHENYL]-3H,6H-1,4,5A,8A-TETRAAZAACE-NAPHTHYLEN-3-ONES AND INTERMEDIATES THEREFOR

[75] Inventors: William T. Cain; Edward Ruso, both of Nanuet, N.Y.; David M. Blum, Upper Saddle River, N.J.; Ian Cutting, Southampton, United Kingdom

[73] Assignee: American Cyanamid Company, Wayne, N.J.

[21] Appl. No.: 10,032

[22] Filed: Jan. 27, 1993

Related U.S. Application Data

[62] Division of Ser. No. 857,892, Mar. 26, 1992.

[51] Int. Cl.$^5$ ................ C07D 487/04; C07D 487/16
[52] U.S. Cl. ...................................... 544/281; 544/251
[58] Field of Search ............................. 544/281, 251

[56] References Cited
U.S. PATENT DOCUMENTS 4,916,137 4/1990 Epstein et al. ........................ 514/267

Primary Examiner—Emily Bernhardt
Attorney, Agent, or Firm—Kenneth J. Dow

[57] ABSTRACT

A novel process for producing 5-[(substituted)amino]-8-[phenyl or substituted-phenyl]-3H,6H-1,4,5a,8a-tetraazaace-naphthylen-3-ones of the formula:

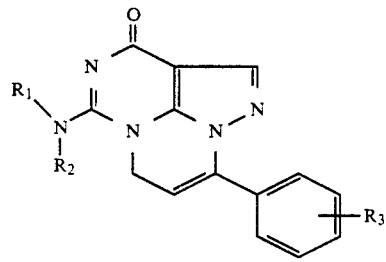

Where $R_1$, $R_2$ and $R_3$ are defined in the specification by reacting a 4,5-dihydro-7-[phenyl or substituted phenyl]-pyrazolo[1,5-a]pyrimidine-3-carboxamide with carbon disulfide and a suitable base and a lower alkyl iodide to give a 5-(lower alkylthio)-8-[phenyl or substituted phenyl]-3H,6H-1,4,5a,8a-tetraazaacenaphthylen-3-one which is further reacted with an amine of the formula:

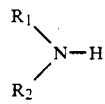

to give the desired compounds is disclosed as well as 5-(loweralkylthio)-8-phenyl-3H,6H,1,4,5a,8a-tetra azaacenaphthylen-3-ones useful as intermediates in the process.

2 Claims, No Drawings

PROCESS FOR THE SYNTHESIS OF 5-[(SUBSTITUTED AMINO]-8-[PHENYL OR SUBSTITUTED-PHENYL]-3H,6H-1,4,5A,8A-TETRAAZAACE-NAPHTHYLEN-3-ONES AND INTERMEDIATES THEREFOR

This is a divisional of co-pending application Ser. No. 07/857,892, filed on Mar. 26, 1992.

BACKGROUND OF THE INVENTION

1. Field of the Invention

The invention relates to a process for the synthesis of 5-[(substituted)amino]-8-[phenyl or substituted-phenyl]-3H,6H-1,4,5a,8a-tetraazaacenaphthylen-3-ones and to the novel 5-(lower alkyl-thio)-8-[phenyl or substituted-phenyl]-3H,6H,1,4,5a,8a-tetraazaacenaphthylen-3-ones useful as intermediates in the process.

2. Description of the Related Art

The 5-(substituted-amino)-8-(phenyl or substituted-phenyl)-3H,6H-1,4,5a,8a-tetraazaacenaphthylen-3-ones as disclosed in U.S. Pat. No. 4,916,137 possess the ability to enhance neural function in warm-blooded animals affected by behavioral neurological problems, including the cognitive deterioration associated with decreased neural function which occurs with cerebral insufficiency, aging, dementia, and similar conditions. In addition synthetic procedures to prepare the 5-(substituted-amino)-8-(phenyl or substituted-phenyl)-3H,6H-1,4,5a-8a-tetraazaacenaphthylen-3-ones are also disclosed. A series of reactions in which a 4,5-dihydro-7-[phenyl or substituted phenyl]-pyrazolo-[1,5-a]pyrimidine-3-carboxamide is reacted with 1,1,-thiocarbonyl-diimidazole in the presence of sodium hydride to prepare 4,5-dihydro-5-thioxo-8-[phenyl or substituted phenyl]3H,6H-1,4,5a,8a-tetraazaacenaphthylen-3-ones which are subsequently reacted with an amine in the presence of aqueous sodium hydroxide and hydrogen peroxide to give the 5-(substituted-amino)-8-[phenyl or substituted-phenyl]-3H,6H-1,4,5a,8a-tetraazaacenaphthylen-3-ones is disclosed.

It has been found that the 5-(substituted-amino)-8-(phenyl or substituted-phenyl)-3H,6H-1,4,5a,-8a-tetraazaacenaphthylen-3-ones can be advantageously synthesized by reaction of 4,5-dihydro-7-[phenyl or substituted-phenyl]pyrazolo[1,5-a]pyrimidine-3-carboxamide with carbon disulfide in the presence of a lower alkyl iodide and suitable base to give the 5-(lower alkyl-thio)-8-[phenyl or substituted-phenyl]-3H,6H-1,-4,5a,-8a-tetraazaacenaphthylen-3-ones which are subsequently reacted with an amine to afford the 5-[(substituted)amino]-8-[phenyl or substituted-phenyl]-3H,6H-1,4,5a,8a-tetraazaacenaphthylen-3-ones.

SUMMARY OF THE INVENTION

The invention provides an improved process for the preparation of 5-[(substituted)amino]-8-[phenyl or substituted-phenyl]-3H,6H-1,4,5a,8a-tetraazaacenaphthylen-3-ones which can be represented by the following structural formula:

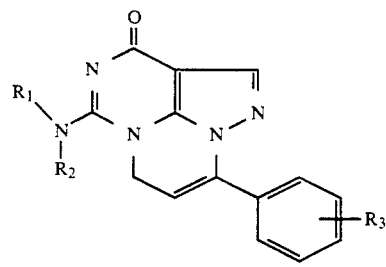

wherein $R_1$ and $R_2$ are each individually selected from the group consisting of hydrogen, branched or unbranched alkyl($C_1$–$C_4$) or benzyl; $R_3$ is hydrogen, halogen, alkyl($C_1$–$C_3$), alkoxy($C_1$–$C_3$) or trifluoromethyl. For the purposes of this invention, halogen may be fluorine, chlorine, bromine or iodine. The improved process comprises reacting a 4,5-dihydro-7-[phenyl or substituted phenyl]-pyrazolo[1,5-a]pyrimidine-3-carboxamide having the formula:

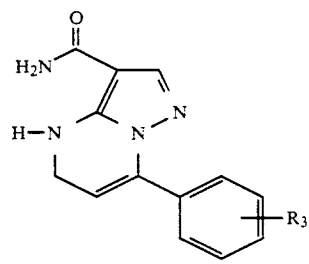

wherein $R_3$ is as defined above with carbon disulfide and a compound of the formula $R_4I$, wherein $R_4$ is defined as lower alkyl($C_1$–$C_3$), to give a xanthate of the formula:

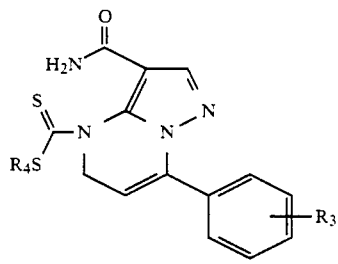

which can be isolated or further reacted in situ to afford a 5-(lower alkylthio)-8-[phenyl or substituted phenyl]-3H,6H-1,4,5a,8a-tetraazaacenaphthylen-3-one having the formula:

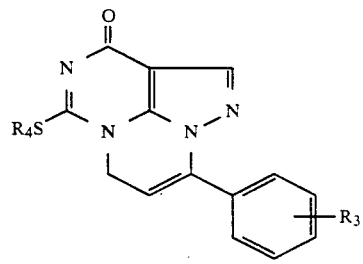

wherein $R_3$ is as defined above, which is subsequently reacted with an amine having the formula:

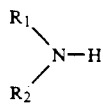

wherein R₁ and R₂ are defined above and recovering the 5-[(substituted)amino]-8-[phenyl or substituted-phenyl]-3H,6H,1,4,5a,8a-tetraazaacenaphthylen-3-one so produced.

DESCRIPTION OF THE PREFERRED EMBODIMENTS

The process and compounds of the present invention are described in the following reaction scheme:

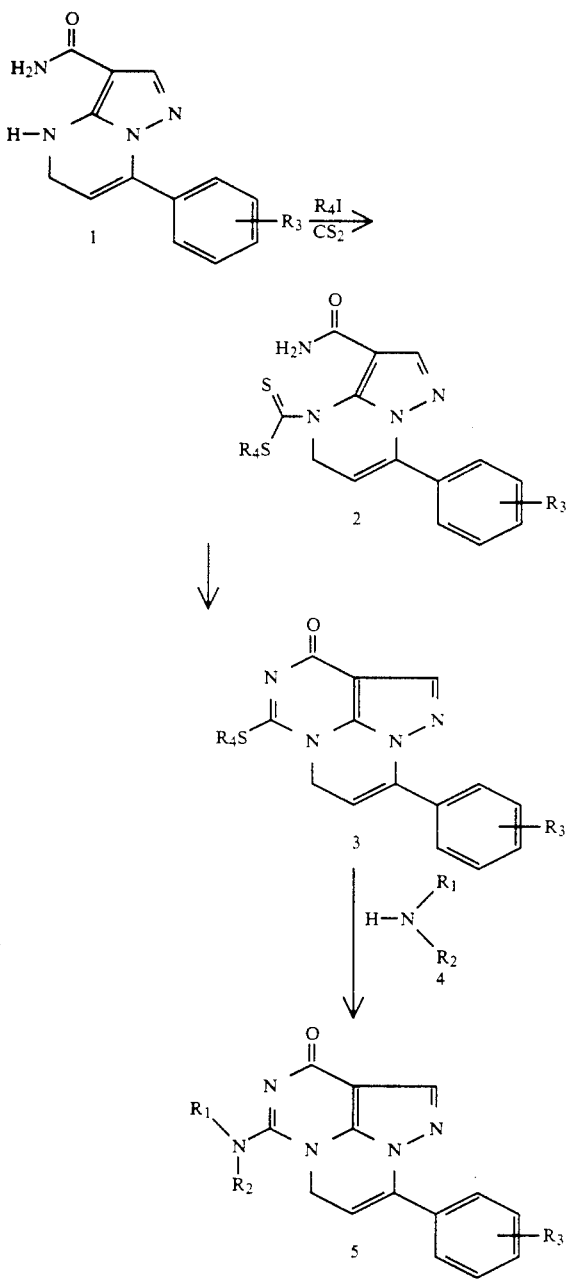

In accordance with the above reaction scheme, 4,5-dihydro-7-phenyl or substituted-phenyl]pyrazolo-1,5-a]pyrimidine-3-carboxamide 1 where R₃ is as described above, is reacted with carbon disulfide in the presence of a suitable base and R₄I, where R₄ is as described above to afford the xanthate 2. This reaction is preferably conducted at temperatures from about −7° C. to about 6° C. for up to one hour. Longer reaction times of up to 18 hours, with the addition of excess base, dilution with ice and water and collection of the solid on a funnel gives the fully closed 5-(lower alkylthio)-8-[phenyl or substituted-phenyl]-3H,6H-1,4,5a,8a-tetraazaacenaphthylen-3-one 3. Suitable bases include sodium hydride, sodium methoxide and potassium t-butoxide but other bases as known in the art may be substituted.

The 5-(lower alkylthio)-8-phenyl or substituted-phenyl]-3H,6H-1,4,5a,8a-tetraazaacenaphthylen-3-one 3 is reacted with amine 4, where R₁ and R₂ are as described above, to yield the final compound, 5. The reaction of 3 with 4 is preferably conducted in a weak acid such as acetic acid at about 80° C. to about 100° C. for about 18 hours. The solution is cooled to room temperature, diluted with ethanol, cooled to 0° C. and the 5-[(substituted)amino]-8-[phenyl or substituted-phenyl]-3H,6H,1,4,5a,8a-tetraaza-acenaphthylen-3-one 5 collected by filtration and dried.

The above process is an improvement over the procedures described in U.S. Pat. No. 4,916,137. As described herein above, the yields of each of the steps are higher and the workup of the reactions are less labor and time intensive.

The following non-limiting examples illustrate the process of the present invention as well as the preparation of the novel compounds.

EXAMPLE 1

5-(Methylthio)-8-[3-(trifluoromethyl)phenyl]-3H,6H-1,4,5a,8a-tetraazaacenaphthylen-3-one A solution of 162 g of 4,5-dihydro-7-[3-(trifluoromethyl)phenyl]pyrazolo[1,5a]-pyrimidine-3-carboxamide in 1.62 L of warm tetrahydrofuran is dried with 40.3 g of anhydrous sodium sulfate, stirred for 3 hours and allowed to stand at room temperature for 18 hours. The mixture is filtered and the cake washed with 200 ml of tetrahydrofuran. The tetrahydrofuran solution is cooled to −3° C. under inert gas. While stirring, 28.4 g of sodium methoxide is added in small portions over a 10 minute period. The temperature is kept from −3° C. to −4.5° C. A solution of 45 ml of carbon disulfide in 45 ml of tetrahydrofuran is added dropwise while keeping the temperature from −7° C. to −4.5° C. The temperature is brought to −1° C. and stirring continued for 35 minutes. A solution of 96 ml of methyl iodide in 96 ml of tetrahydrofuran is added dropwise over 20 minutes while maintaining the temperature from −1° C. to +4° C. Following an additional 1 hour of stirring, 56.7 g of sodium methoxide is added portionwise over 20 minutes under inert gas while keeping the temperature from −8° C. to 6° C. Following each portionwise addition the temperature rose to 6° C. The reaction mixture is stirred at room temperature for 18 hours. The reaction mixture is diluted with 3.0 L of water and 600 g of ice. The solid is collected on a filter and the cake washed with 3×500 ml of water then dried to give 160.5 g of the desired product. The collected solid is stirred with a solution of 700 ml of n-heptane and 1400 ml of ethyl acetate for 1 hour then collected by filtration. The cake is washed with 3×160 ml of (2:1) ethyl acetate:n-heptane and dried to afford 105 g (54.8%) of the desired product.

EXAMPLE 2

5-(Methylthio)-8-[3-(trifluoromethyl)phenyl]-3H,6H-1,4,5a,8a-tetraazaacenaphthylen-3-one A solution of 1055 g of 4,5-dihydro-7-[3-(trifluoromethyl)-phenyl]pyrazolo[1,5a]pyrimidine-3-carboxamide in 9 L of tetrahydrofuran is stirred with 263.4 g of sodium sulfate of 0.5 hours and allowed to stand at room temperature overnight. The reaction mixture is filtered and the cake washed with tetrahydrofuran (3×250 ml). The filtrate is cooled to −3.5° C. and 136.5 g of a 60% dispersion of sodium hydride in mineral oil added over a 30 minute period while maintaining the temperature from −3.5° C. to 4° C. The solution is stirred about 20 minutes at 0° C. to +4° C. and a solution of 272.2 g of carbon disulfide in 215 ml of tetrahydrofuran added dropwise over a 22 minute period while an orange solid precipitates. The reaction mixture is stirred for 20 minutes at 2° C. to −3.5° C. followed by the addition of a solution of 1453 g of methyl iodide in 637 ml of tetrahydrofuran dropwise over 40 minutes while maintaining the temperature from −3.5° C. to 1° C. The reaction mixture is stirred 1.5 hours at −5° C. to −8° C., while maintaining the temperature below 2° C., 237 g of sodium hydride is added portionwise over 2.75 hours. The reaction mixture is stirred overnight while warming to room temperature. The reaction mixture is diluted with 250 ml of ethanol, 16 L of water, 3.82 kg of ice and stirred for 1 hour. The resulting solid is collected by filtration and then slurried with 9 L of ethyl acetate and 4.5 L of heptane for 1 hour. The solid is collected by filtration and washed with a 2:1 ethyl acetate-heptane (3×1 L) solution, dried at 23 mmHg at 40° C. to afford 648 g (75%) of the desired product.

EXAMPLE 3

5-(Methylthio)-8-[3-(trifluoromethyl)phenyl]-3H,6H-1,4,5a,8a-tetraazaacenaphthylen-3-one A solution of 3.18 kg of 4,5-dihydro-7-[3-(trifluoromethyl)-phenyl]pyrazolo[1,5-a]pyrimidine-3-carboxamide in 30 L of tetrahydrofuran is cooled to 2.8° C. under nitrogen and stirred while 1370 g of potassium tert-butoxide is added portionwise over 25 minutes while maintaining a temperature less than 4° C. The reaction mixture is stirred at −6.2° C. for 45 minutes. To the reaction mixture is added 850 g of carbon disulfide through a dropping funnel over a 10 minute period while maintaining the temperature below 2° C. The funnel is rinsed with 500 ml of tetrahydrofuran and the reaction mixture allowed to stir for 45 minutes. While maintaining the temperature from −8° C. to 3.2° C., 1870 g of methyl iodide is added dropwise through a dropping funnel. The funnel is rinsed with 500 ml of tetrahydrofuran and the reaction mixture allowed to stir for 1 hour. An additional 3804 g of methyl iodide is added. The reaction mixture is stirred for 50 minutes while cooling to −23.1° C. An additional 2530 g of potassium tert-butoxide is added over 2 hours while maintaining a temperature of −23.1° C. to 10.0° C. After half of the potassium tert-butoxide is added another 300 ml of methyl iodide is added. The remaining potassium tert-butoxide is added and the reaction mixture stirred while warming to room temperature overnight. The reaction mixture is diluted with 3 kg of ice and 10 L of water then added to 80 L of water with stirring. The reaction flask is rinsed with 26 L of water which is added to the ice and water containing the original reaction mixture. Stirring is continued for 40 minutes and the solids collected by filtration. The filter cake is washed with 20 L of water and dried at 30 mm Hg, 35° C. to afford 3.4 kg (90%) of the desired product.

EXAMPLE 4

3-(Aminocarbonyl)-7-[3-(trifluoromethyl)-phenyl]-pyrazolo[1,5-a]pyrimidine-4(5H-carbodithioic acid methyl ester A solution of 3.0 g of 4,5-dihydro-7-[3-(trifluoromethyl)phenyl]pyrazolo-[1,5a]pyrimidine-3-carboxamide in 30 ml of tetrahydrofuran is cooled to 0° C. While stirring, 0.40 g of a 60% dispersion of sodium hydride is added and stirring continued at 0° C. for 30 minutes. While maintaining the temperature at 0° C., 1.11 g of carbon disulfide is added dropwise at a rate to maintain the temperature. Following 30 minutes of stirring the temperature is lowered to −7° C. and 2.07 g of methyl iodide is added at a rate to maintain the temperature at −7° C. to −4° C. The reaction mixture is allowed to warm to room temperature and stir overnight. While stirring, 66 g of ice water is added with continued stirring over 20 minutes. The solid is collected, washed with water (3×25 ml), hexane (3×25 ml) and air dried to provide 3.5 g (90%) of the desired product.

EXAMPLE 5

5-[(Phenylmethyl)amino]-8-[3-(trifluoromethyl)-phenyl]-3H,6H-1,4,5a,8a-tetraazaacenaphthylen-3-one To a suspension of 5.0 g of 5-(methylthio)-8-[3-(trifluoromethyl)phenyl]-3H,6H-1,4,5a,8a-tetraazaacenaphthylen-3-one in 35 ml of acetic acid is added 4.78 g of benzylamine. The reaction mixture is heated on a steambath for 18 hours. The solution is cooled to room temperature and 17 ml of ethanol is added followed by cooling to 10° C. An additional 35 ml of ethanol and 20 g of ice are added and the resulting slurry stirred for 30 minutes at 0° C. The product is collected by filtration, washed with ethanol (2×20 ml) and dried at 40° C./30 mm Hg to give 3.6 g (62.1%) of the desired product.

EXAMPLE 6

5-[(1-Methylethyl)amino]-8-[3-(trifluoromethyl)-phenyl]-3H,6H-1,4,5a,8a-tetraazaacenaphthylen-3-one To a suspension of 5.0 g of 5-(methylthio)-8-[3-(trifluoromethyl)phenyl]-3H,6H-1,4,5a,8a-tetraazaacenaphthylen-3-one in 35 ml of acetic acid is added 2.64 g of isopropylamine. The reaction mixture is heated on a steambath for 18 hours. The resulting solution is cooled to room temperature and 17 ml of ethanol added. The mixture is cooled to 10° C. and 35 ml of ethanol and 20 g of ice added. The mixture is stirred for an additional 30 minutes at −10° C. The product is collected by filtration, washed with ethanol (2×20 ml) and air-dried to give 3.2 g (62.3%) of the desired product.

EXAMPLE 7

5-[(2-Methylpropyl)amino]-8-[3-(trifluoromethyl)-phenyl]-3H,6H-1,4,5a,8a-tetraazaacenaphthylen-3-one To 11.1 L of acetic acid is added 2.23 kg of isobutylamine dropwise, under nitrogen over 0.75 hour at a rate such that the temperature does not go above 45° C. The temperature is controlled with external cooling. Following complete addition, 2.78 kg of 5-(methylthio)-8-[3-(trifluoromethyl)phenyl]-3H,6H-1,4-5a,8a-tetraazaacenaphthylen-3-one is added. The reaction mixture is heated at 95° C. for 18 hours. The reaction mixture is cooled to 45° C. and transferred to a larger vessel with an additional glacial acetic acid wash (2×500 ml). While stirring, 22.2 L of ethanol and 11.1 kg of crushed ice is added. Stirring is continued for 1 hour, the solid collected and washed with (3×2 L) of 2:1 ethanol water to afford 2.82 kg (90.7%) of the desired product as a dried solid.

We claim:

1. A compound of the formula:

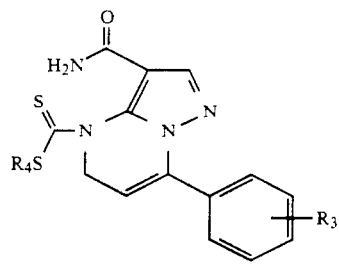

wherein $R_3$ is selected from the group consisting of hydrogen, halogen, alkyl($C_1$-$C_3$), alkoxy($C_1$-$C_3$) or trifluoromethyl and $R_4$ is lower alkyl($C_1$-$C_3$).

2. The compound according to claim 1, 3-(aminocarbonyl)-7-[3-(trifluoromethyl)phenyl]pyrazolo-[1,5-a]pyrimidine-4(5H)-carbodithioic acid methyl ester.

* * * * *